United States Patent [19]

Mayer et al.

[11] 4,064,011

[45] Dec. 20, 1977

[54] PROCESS FOR PRODUCING ECORI RESTRICTION ENDONUCLEASE WITH E.COLI MUTANTS

[75] Inventors: Hubert Mayer; Horst Schutte, both of Wolfenbuttel, Germany

[73] Assignee: Gesellschaft fur Biotechnologische Forschung mbH, Braunschweig-Stockheim, Germany

[21] Appl. No.: 778,261

[22] Filed: Mar. 16, 1977

[51] Int. Cl.$^2$ .............................................. C12D 13/10
[52] U.S. Cl. .................................... 195/65; 195/66 R
[58] Field of Search .......................... 195/62, 65, 66 R

[56] References Cited

PUBLICATIONS

Smith in Methods in Molecular Biology, vol. 7, 1974, pp. 71–85.

Primary Examiner—Lionel M. Shapiro
Attorney, Agent, or Firm—Scully, Scott, Murphy & Presser

[57] ABSTRACT

ECoRI restriction endonuclease is produced with certain mutant strains of E.coli which are not antibiotic resistant and do produce the said enzyme which is obtained from the E.coli mutant cells without destroying the cells by extraction procedures.

8 Claims, No Drawings

PROCESS FOR PRODUCING ECORI RESTRICTION ENDONUCLEASE WITH E.COLI MUTANTS

The ECoRI restriction endonuclease has become of great importance in DNA analysis, since it shows a high substrate specificity. The specific double-strand point of recognition is of the following sequence:

5'--A/T-G-A-A-T-T-C-A/T- - 3'

3'--T/A-C-T-T-A-A-G-T/A- - 5'

This is characterised in that it produces overlapping single strand ends. DNA fragments, which are split by "ECoRI", are capable of being re-associated at their ends and linked with polynucleotide ligases. This operating procedure allows DNA fragments of procaryotic and eucaryotic origin to attach to repeatable DNA, such as plasmide DNA or phage DNA. The DNA fragments re-combined in vitro can be transferred by transformation or transfection into bacteria cells and multiplied. It thus becomes possible to solve the problem of channelling new genetic data into bacteria. By systematic selection of the DNA to be introduced, it is possible by this process for bacteria to be so changed genetically that they produce important natural substances.

It is known from "Nature" 214, 885–887 (1967) that the antibiotic resistance factor R1, an $fi+$ factor, in *Escherichia coli*, codes resistance to chloramphenicol, canamycin, streptomycin, ampicillin and sulphonamides, and it is also known from J. Bacteriol. 112, 1275–1279 (1972) that it determines the synthesis of the ECoRI restriction endonuclease ECoRI. Furthermore, a deletion mutant of this R1 factor is generally known, which is resistant to canamycin; this is called R1drd16. A process for the preparation of the ECoRI restriction endonuclease is known from "Methods in molecular biology", New York, Marcel Dekker Inc., vol. 7, 67–105 (1974), in which, to release the enzyme, the cells are destroyed and multi-stage precipitation steps are required for isolation thereof.

The process according to the present invention is predicated on the use of a bacterium which is not resistant to antibiotics and the enzyme is released without destruction of the cells and, thereafter, a single-stage precipitation is required for isolation of the enzyme.

In accordance with the present invention, certain mutant strains of *E.coli* which have no antibiotic resistance but do synthesize ECoRI restriction endonuclease are aerobically cultivated in aqueous nutrient media containing protein carbon-source and inorganic salts to produce a submerged culture of the organism; the cultured organism is separated from the medium and the enzyme extracted from the cells by standard extraction techniques e.g. by stirring in an aqueous salt solution at or near a pH of 7, preferably buffered to maintain substantially neutral pH, and the enzyme is recovered from the aqueous salt solution by standard techniques preferably in the form of an aqueous concentrate.

In a preferred mode of the invention, *Escherichia coli*, SB5, DSM (Deutsche Sammlung von Microorganismen) No. 686, which has no antibiotic resistance, but does accumulate ECoRI restriction endonuclease, is cultivated under aerobic conditions in an aqueous nutrient growth medium at a temperature of from about 30° to about 40° C until substantial growth takes place, usually up to the late logarithmic phase. Thereafter the mature cells are separated from the nutrient medium, as by filtering or centrifuging, and the enzyme extracted from the cells by stirring, preferably at high shear, in an aqueous salt solution, which preferably contains a non-ionic detergent. To preclude loss of enzyme activity, it is preferred to conduct the extraction at low temperatures, e.g. from about 0° to about 4° C. The aqueous salt solution, usually 0.1MNaCl, is generally buffered to a pH at or near neutral employing standard buffers, e.g. PEM (10 mM.KH$_2$PO$_4$—K$_2$HPO$_4$,pH7.0,0.7mM. mercaptoethanol and 1mM EDTA), for best results. The cells are separated from the aqueous salt solution and the solution is then treated to remove interfering activities also extracted along with the endonuclease, e.g. by addition of cetyl trimethyl ammonium bromide to precipitate the said activities which are separated from the salt solution, e.g. by centrifugation and decantation, to obtain the solution containing the endonuclease.

The enzyme solution can be further purified by adsorption onto known adsorbents such as phosphorylated cellulose and then eluted, for example, with aqueous sodium chloride gradients (0.3–0.8M), and the active fractions combined. For further purification, the combined fractions can be further purified by adsorption onto hydroxylapatite column and eluted with aqueous phosphate salt gradients (0.01–0.5M). The active fractions are combined and, for convenience, can be concentrated using, for example, an ultrafilter membrane.

The process is applicable regardless of the amount of cells to be extracted and is effective with quantities of about 0.5–500 g. of the cells and even with quantities larger than 500 g. In the latter case, it is convenient to employ spheres of, for example, glass, ceramics or plastic in treating the cells to release the desired enzyme from the cells.

The desired mutant of *E.coli* SB5 is prepared, for example, in accordance with the following procedure:

The factor R1drd16, which is resistant to canamycin, was transferred into an endonuclease producing I-negative *E.coli* strain 1100. By mutation with N-nitroso-N-methyl-N'Nitroguanidine (NNMG), colonies free from antibiotic resistance were obtained, these being called R1drd16 mut 1. From the RY 13 strain, known from "Methods in Molecular Biology", loc. cit., the factor which determines the "ECoRI" was isolated and transformed into the *E.coli* 1100 R1drd16 mut 1 strain. Then, there were isolated those colonies which are not antibiotic resistant but produced "ECoRI".

The bacterium SB5 used in the process according to the invention has been lodged at the Deutsche Sammlung von Microorganismen (German Collection of Microorganisms) with the DSM No. 686. The strain shows properties such as those of K12 strains of Escherichia coli in Bergey's Manual of Determinative Bacteriology, 8th Edition. The strain is sensitive to chloramphenicol, canamycin, streptomycin, ampicillin and sulphonamide, and synthesizes ECoRI restriction endonuclease.

The invention is further illustrated by the following example:

EXAMPLE

The SB5 strain was initially placed for about 6 hours in 300 ml. of medium at 37° C while shaking. A 20 liter fermenter, sterilised for 30 minutes at 121° C., was initially inoculated with the pre-culture. The culture was allowed to grow at 37° C, with an aeration of 1000 liters (at n.t.p.) and a speed of rotation of 600 rpm of a tumbler-type stirrer system for 5 to 6 hours. The 20 liters of pre-culture were thereafter pumped over -3-in sterile form into a 200 liter fermenter previously sterilized for 60 minutes at 121° C. A pH value of 6.8 to 7 was established by titration with 4 liters of 25% NH$_4$OH, interval time 20 seconds, dosage time 2 seconds, temperature 37° C., aeration 1100 liters (at n.t.p.), rotational speed 900 rpm., initial OD$_{578}$ = 1.250; after a growing time of 8½ hours, the fermentation process was stopped at OD$_{578}$ of 22,000. After cooling to about 20° C., removal by centrifuging was carried out. Total bacteria moist mass: 7,550 g. with approximately 89% water content.

The cells were frozen in aliquots of 1000 g. at $-20°$ C.

With the isolation of the enzyme by mechanical agitation in small amounts, 0.5 g. of moist cell mass, in fresh form or thawed after freezing, with 3 ml. of PEM buffer (PEM contains: 10mM of KH$_2$PO$_4$ — K$_2$HPO$_4$, pH 7.0, 0.7 mM of 2-mercaptoethanol and 1 mM of EDTA) and 0.1 m NaCl and 0.1 mM of PMSF and 0.2% of non-ionic detergent (Triton N101 — commercial product of Rohm & Haas, Frankfurt)), was stirred on a homogeniser (Potter-Elvehjen type) for 2 × 2.5 minutes, with cooling by ice, at 2,000 rpm. After centrifuging (Beckmann JA10 type, 10,000 rpm., 2° C for 1 hour), the activity in the supernatant layer was tested; in amounts of average size, up to 500 g. of moist cell mass, fresh or thawed after freezing, were suspended with 500 ml. of PEM buffering agent, 0.1 mM of PMSF, 0.2 m. of NaCl and 0.2% of non-ionic detergent. After several passages through the homogeniser, in accordance with Bioch. No. 9, 2932-2938 (1966), with cooling by ice, removal by centrifuging was carried out as above and the activity in the supernatant layer was established. In large quantities, of more than 500 g. of moist cell mass, fresh or thawed after freezing, the enzyme activity was detached with mechanically agitated glass beads (Dyno Muhle type- Messrs. Bachofen, Basle, Switzerland).

a. size of grinding container: 0.6 liter for continuous operation;
b. grinding elements, type and size: glass balls, lead-free, 1–1.5 $\phi$;
c. Quantity of grinding elements: 520 ml.;
d. Speed of rotation of stirrer shafts: 2000 rpm.;
e. Wall-disc material: glass, lead-free/stainless steel;
f. Throughflow quantity per hour: 5-7 1/h;
g. passages: 2;
h. size of the microseparator: 0.2 or 0.3 mm.
i. cooling jacket temperature: $-4°$ C to $-8°$ C.

Centrifuging followed (Beckmann type JA10 at 1000 rpm; 2° C for 1 hour). Activity in the supernatant layer was determined.

Phosphocellulose P11 (from Messrs. Whatman) was stirred into the clear supernatant layer, which has been equilibrated beforehand with PEM, 0.1 mM of PMSF and 0.1 m of NaCl. The cellulose was filtered off with suction, using a suction filter, and subsequently washed with the PEM buffering agent. "ECoRI" was eluted with the PEM buffering agent and 1 M NaCl. The eluate was concentrated with an ultrafilter membrane (Amicon hollow fibre, type H1P10) and dialysed against PEM buffering agent in 0.1 M NaCl. The activity of "ECoRI" was determined. The dialysate was pumped on to a column of phosphocellulose, which was washed with PEM buffering agent and 0.1 M NaCl and eluted with a linear gradient of 0.3–0.8 M NaCl. The activity eluted between 0.45 and 0.8 M NaCl.

A hydroxyl apatite column was equilibrated with PEM buffering agent and 0.1 M NaCl. After supply of the active fractions, washing was effected with the same buffering agent and elution was carried out with a linear gradient of 0.01 M–0.5 M KPO$_4$, pH 7. The recovered ECoRI restriction endonuclease is highly active and free from unspecific enzyme activities.

The "ECoRI" can be stored in a refrigerator at 4° C with ice cooling, with and without 50% glycerol; with 50% glycerol, it can be stored in stable form at $-20°$ C.

With the detachment or dissolution stage, an approximately 50% yield of enzyme activity is achieved; there is the technical advantage that, firstly, a high specific activity is obtained and, secondly, the undestroyed cell mass can be supplied for further use, for example, in order to recover intracellular substances. A 10% cetyl trimethyl ammonium bromide solution was added to the supernatant substance with constant stirring up to a final concentration of 1% by volume. After stirring for 30 minutes, centrifuging was carried out as indicated above and the precipitate was discarded.

The ECoRI restriction endonuclease produced by the process of the invention was tested as regards its activity in accordance with "Methods in Molecular Biology", loc.cit. The following values were obtained: Col E1-DNA was split once and λDNA six times. A modified activity of "ECoRI" was found in accordance with PNAS 72, 3310–3314 (1975).

In the foregoing, PMSF is phenylmethylsulfonyl chloride and EDTA is ethylendiaminetetraacetic acid.

As employed in this disclosure and in the appended claims, the designation "*E. coli*" refers to an organism formally known as *Escherichia coli*.

What we claim is:

1. A process of producing ECoRI restriction endonuclease which comprises cultivating *E.coli* SB5, DSM No. 686 in an aqueous nutrient medium therefor and recovering said enzyme from the cultivated cells.

2. Process according to claim 1 wherein the said recovery is accomplished by extraction of the enzyme from the cultivated cells with aqueous sodium chloride solution.

3. Process according to claim 2 wherein said sodium chloride solution is buffered to a pH of about 7.

4. Process according to claim 3 wherein the extraction is accomplished by high shear stirring of the cells in the buffered sodium chloride solution, the cells are separated and the resulting solution is freed of interfering activities by addition of cetyl trimethylammonium bromide following by removal of the precipitated activities to obtain the solution containing the endonuclease.

5. Process according to claim 4 including the further step of adsorbing the endonuclease onto phosphorylated cellulose adsorbent followed by elution with aqueous sodium chloride solution.

6. Process according to claim 5 including the further step of adsorbing the endonuclease onto hydroxyapatite adsorbent followed by elution with aqueous phosphate salt solution to obtain purified endonuclease in the eluate.

7. Process according to claim 5 wherein the elution with aqueous sodium chloride is accomplished employing salt gradient concentrations of from 0.3 to 0.8M.

8. Process according to claim 6 wherein the elution with aqueous phosphate salt is accomplished employing salt gradient concentrations of from 0.01 to 0.5 M.

* * * * *